United States Patent [19]

Kim

[11] 4,066,640
[45] Jan. 3, 1978

[54] METHAMPICILLIN LYSINATE AND ITS METHOD OF MANUFACTURE

[76] Inventor: Young Sul Kim, 302-62, Yichon-dong, Yong San, Seoul, South Korea

[21] Appl. No.: 762,663

[22] Filed: Jan. 26, 1977

Related U.S. Application Data

[62] Division of Ser. No. 709,644, July 29, 1976, Pat. No. 4,031,076.

[30] Foreign Application Priority Data

July 31, 1975  South Korea ..................... 1686/75

[51] Int. Cl.$^2$ ........................................... C07D 499/44
[52] U.S. Cl. .................................................. 260/239.1
[58] Field of Search ..................................... 260/239.1

[56] References Cited

U.S. PATENT DOCUMENTS

| 3,198,788 | 8/1965 | Granatek | 260/239.1 |
| 3,886,140 | 5/1975 | Lee | 260/239.1 |

*Primary Examiner*—Gerald A. Schwartz
*Attorney, Agent, or Firm*—Armstrong, Nikaido & Marmelstein

[57] ABSTRACT

Water soluble Methampicillin Lysinate is disclosed along with a method of making the compound. The compound of the invention has superior stability and, because of its greater solubility, has a high rate of absorption into the gastrointestinal tract.

Methampicillin Lysinate is prepared by converting ampicillim to methylene-ampicillin which is reacted with L-Lysine to produce the compound of the invention.

1 Claim, No Drawings

METHAMPICILLIN LYSINATE AND ITS METHOD OF MANUFACTURE

This is a division of application Ser. No. 709,644 filed July 29, 1976 now U.S. Pat. No. 4,031,076.

The present invention is directed to a new form of ampicillin having superior water solubility and utility as an antibiotic and to a method of manufacturing this compound which is identified as methampicillin lysinate.

As originally discovered, penicillin-G had the disadvantages of chemical instability which affected its activity and also the fact that its use as an antibiotic was limited to gram-positive bacteria. Subsequent discovery of ampicillin, which was derived from 6-amino penicillanic acid, provided an antibiotic having greater stability then penicillin-G and also which was effective against gram-negative bacteria.

Unfortunately, these forms of penicillin have continued to have some of the deleterious side effects of natural penicillin and also a low solubility in water. Thus, the solubility of ampicillin or methampicillin is relatively low and this lack of solubility has an adverse effect upon the absorption of the antibiotic into the gastro-intestinal tract.

Therefore, it is an object of the present invention to provide a new form of ampicillin having substantially greater water solubility and stability than either ampicillin or methampicillin which has been known in the prior art.

According to the present invention, it has been discovered that a new form of methampicillin, which will be described hereinafter, and which is known as methampicillin lysinate, has a high water solubility which is approximately 3.4 times as great as ampicillin trihydrate. Thus, the compound of the present invention has the advantage of being readily available in liquid form and also of having a high absorption rate through the gastro-intestinal tract.

The compound of the present invention is a derivative of methylene ampicillin in which the 5'-amino-5'-carboxyl pentyl amino methyl radical is substituted at the amino position on the α-amino benzyl radical of 6-amino penicillanic acid. Its chemical structure and molecular formula are as follows:

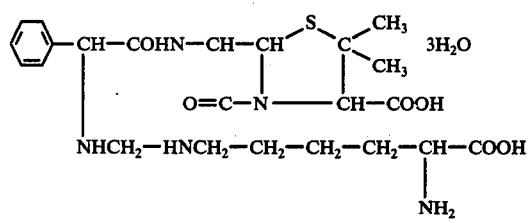

The trihydrate is a white needle crystalline powder having the formula: $C_{23}H_{33}O_6N_5S \cdot 3H_2O$. The chemical name of this compound is D - (—) - 6 - [IO - ( N - 5' amino - 5' carboxylpentyl amino methyl ) - amino phenyl acetamide] - 3.3 - dimethyl - 7 - oxo - 4 - thio - 1 azabicycleheptane - 2 carboxylic acid trihydrate, but has been named ampicillin methylene lysinate or methampicillin lysinate because L-lysine is attached to methylene aminobenzyl penicillanic acid and given the general name methampicillin lysinate.

Methampicillin lysinate is synthesized by a series of procedures. In the first step, formaldehyde is reacted with ampicillin to produce methylol - ampicillin which is quickly converted to methylene ampicillin as described below. In the first step, in order to make the ampicillin, which is only slightly soluble, water-soluble it is converted into sodium ampicillinate by the addition of sodium carbonate or sodium bicarbonate at a temperature of 7°–10° C and pH 7.0–8.0, using a concentration of 0.001 mole ampicillin and 0.01 mole sodium bicarbonate. After making the ampicillin water soluble, a 37 to 40 percent formaldehyde solution is reacted with the ampicillin in about a ION-formalin solution since the concentration effects the yield.

In the next step of the procedures, L-lysine, one of amino acids is reacted with the intermediate product which is obtained in the first step to obtain methampicillin lysinate, which is the end product of the synthesis.

The following are the chemical formulas and procedures of the reaction.

Synthesis of methampicillin lysinate

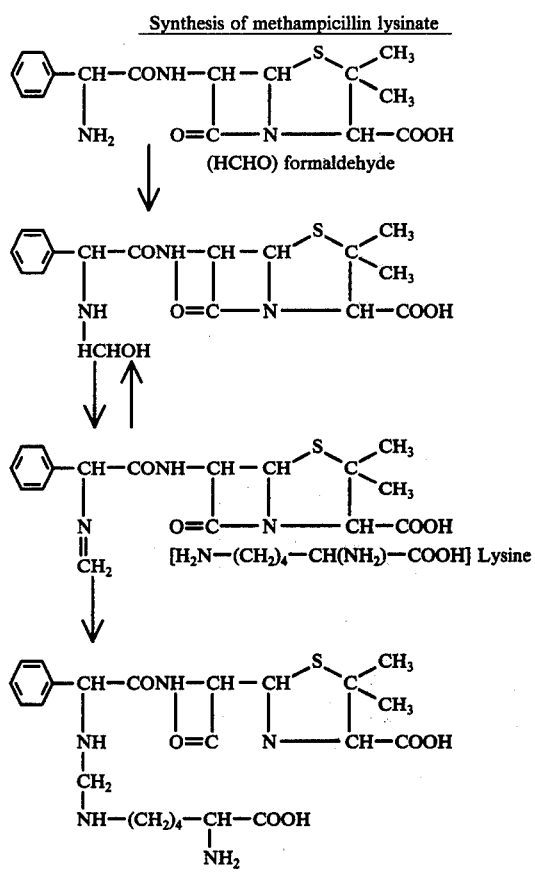

EXAMPLE A

A suspension of ampicillin (19.50 gm) in the water (1,000 ml) was cooled to 5° C, stirred slowly for 30 minutes to make a homogenious sludge and a pH 7 to 8 obtained by adding 10% sodium bicarbonate solution (51 ml).

A mixture of this solution and formalin (5.8 ml) containing more than 37 percent of formaldehyde was stirred for 1 hour continuously. Then L-lysin (8.05 gm) was added with stirring over 1 hour and acidified with hydrochloric acid (7.0 ml) to produce a pH of 2.5 to 3.0. A white crystallined precipitate, of methampicillin L-lysinate was obtained. The precipitate was filtered subsequent to the resulting mixture being allowed to stand at 0° C for 24 hours, washed with dry aceton and then dried below 40° C to yield 54.9% of a white powder, having M.P. of 197° to 198°.

The methampicillin L-lysinate produced by the present invention is soluble in water, but insoluble in ethanol and chloroform. The solubility in acetic acid is 25 mg per a ml and in dimethyl-formamide, 8 mg/per a milliliter.

The specific optical rotation is $[\alpha]_d^{20} = 240\ (C=0.25)$, and Rf 0.765 on the thin layer chromatography on silica gel using as a solvent 5% acetic acid and 95% acetone and conventional procedures.

What is claimed is:

1. A process for preparing Methampicillin Lysinate having the formula:

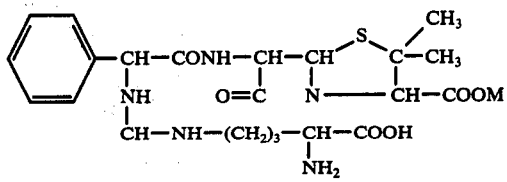

wherein M is selected from the group consisting of hydrogen, sodium, potassium, calcium and aluminum, which comprises the steps of:
   a. solubilizing ampicillin by converting ampicillin to a water saluble salt;
   b. reacting said water soluble salt of ampicillin with a solution of formaldehyde and formalin to produce methylene ampicillin;
   c. reacting L-Lysine with said methylene ampicillin in acid solution to obtain Methampicillin Lysinate.

* * * * *